United States Patent
Lin et al.

(10) Patent No.: US 9,678,033 B2
(45) Date of Patent: Jun. 13, 2017

(54) ELECTROCHEMICAL BIOSENSOR AND METHOD FOR PRODUCING THE SAME

(71) Applicant: TAIWAN GREEN POINT ENTERPRISES CO., LTD., Taichung (TW)

(72) Inventors: Yu-Chuan Lin, Taichung (TW); Sung-Yi Yang, Taichung (TW); Yi-Cheng Lin, Taichung (TW)

(73) Assignee: Taiwan Green Point Enterprises Co., Ltd., Taichung (TW)

( * ) Notice: Subject to any disclaimer, the term of this patent is extended or adjusted under 35 U.S.C. 154(b) by 0 days.

(21) Appl. No.: 14/580,799

(22) Filed: Dec. 23, 2014

(65) Prior Publication Data

US 2015/0185178 A1 Jul. 2, 2015

(30) Foreign Application Priority Data

Dec. 26, 2013 (TW) .............. 102148419 A

(51) Int. Cl.
*G01N 27/327* (2006.01)
*B01L 3/00* (2006.01)

(52) U.S. Cl.
CPC .......... *G01N 27/327* (2013.01); *B01L 3/5027* (2013.01); *G01N 27/3272* (2013.01); *B01L 2200/12* (2013.01); *B01L 2300/0645* (2013.01); *B01L 2300/0663* (2013.01)

(58) Field of Classification Search
None
See application file for complete search history.

(56) References Cited

U.S. PATENT DOCUMENTS

| 4,626,324 A * | 12/1986 | Samuels ................. C25D 3/56 205/125 |
| 8,840,776 B2 | 9/2014 | Hsu |
| 2002/0195345 A1* | 12/2002 | Bentsen .......... G01N 27/44791 204/600 |
| 2003/0132828 A1 | 7/2003 | Hashimoto et al. |
| 2003/0178229 A1* | 9/2003 | Toyoda ................. H01L 21/486 174/261 |

(Continued)

FOREIGN PATENT DOCUMENTS

| CN | 1395734 A | 2/2003 |
| CN | 1854728 A | 11/2006 |

(Continued)

*Primary Examiner* — Matthew Martin
*Assistant Examiner* — Steven E Rosenwald
(74) *Attorney, Agent, or Firm* — Volpe and Koenig, P.C.

(57) ABSTRACT

An electrochemical biosensor includes a substrate, a plurality of layered active metal parts, a plurality of layered electrodes, a reaction confinement layer, an electrochemical reactive layer and a cover piece. The substrate is formed with through holes each of which is defined by an interior wall surface and penetrates top and bottom surfaces. Each of the layered active metal parts is formed at least upon a respective one of the interior wall surfaces. The layered electrodes are formed on the layered active metal parts. The reaction confinement layer confines a reactor space over a region where the through holes are formed. The electrochemical reactive layer is disposed in the reactor space and is electrically coupled to the layered electrodes.

4 Claims, 10 Drawing Sheets

(56) References Cited

U.S. PATENT DOCUMENTS

| | | | | |
|---|---|---|---|---|
| 2006/0175199 A1* | 8/2006 | Huang | ................... | C12Q 1/001 204/400 |
| 2012/0073966 A1* | 3/2012 | Hsu | ................... | G01N 27/3272 204/400 |
| 2013/0098775 A1* | 4/2013 | Pei | ........................ | C12Q 1/006 205/777.5 |

FOREIGN PATENT DOCUMENTS

| | | | | |
|---|---|---|---|---|
| JP | 09-166571 | * | 6/1997 | ........... G01N 27/327 |
| TW | 201331577 A | | 8/2013 | |

* cited by examiner

ELECTROCHEMICAL BIOSENSOR AND METHOD FOR PRODUCING THE SAME

CROSS-REFERENCE TO RELATED APPLICATION

This application claims priority of Taiwanese Patent Application No. 102148419, filed on Dec. 26, 2013.

FIELD

Embodiments of the invention generally relates to biosensors and methods for producing the same, and more particularly to electrochemical biosensors and methods for producing the same.

BACKGROUND

Referring to FIG. 1, an electrochemical biosensor 8 is adapted for measuring concentration of an analyte in a sample liquid, such as blood sugar concentration in a blood sample, or the concentration of heavy meal pollutants in a wastewater sample. As shown in FIG. 1, the electrochemical biosensor 8 includes an insulating substrate 81, a metallic conductive layer 82 formed on the insulating substrate 81 by printing, an insulating layer 83 disposed to partially expose the metallic conductive layer 82, a reagent-reactive layer 84 in electrical contact with the metallic conductive layer 82, and a cover plate 85. Although the electrochemical biosensor 8 may achieve the primary goal of measuring the analyte concentration in the sample liquid, the metallic conductive layer 82, which is formed by screen printing, may exhibit relatively high electrode impedance which results in attenuation and interference of electrical output signals. In addition, the metallic conductive layer 82 of the electrochemical biosensor 8 may consume a relatively large amount of metallic raw material which increases the production cost.

Referring to FIG. 2, another electrochemical biosensor 9 is shown to include an insulating substrate 91, a pair of electrodes 92, an electrochemical reactive layer 93 and a cover plate 94. The insulating substrate 9 is formed with a reaction chamber 911 and a pair of through holes 912 in spatial communication with the reaction chamber 911. The electrodes 92 are respectively disposed in the through holes 912, and the electrochemical reactive layer 93 is disposed in the reaction chamber 911 to be electrically coupled with the electrodes 92. The cover plate 94 is disposed to cover the reaction chamber 911. Although the electrochemical biosensor 9 may also achieve the primary function of measuring the analyte concentration in the sample liquid, the electrodes 92 and the substrate 91 are separately made, and a relatively complicated assembling procedure is therefore required. In addition, such configuration of the electrochemical biosensor 9 requires relatively low tolerance in making the electrodes 92 and the through holes 911 and thereby increases the production cost.

SUMMARY

Certain embodiments of the present invention provide electrochemical biosensors that may alleviate the aforementioned drawbacks, and/or methods for producing the same.

According to an aspect of the present invention, an electrochemical biosensor may include a substrate, a plurality of layered active metal parts, a plurality of layered electrodes, a reaction confinement layer, an electrochemical reactive layer and a cover piece.

The substrate is made of an electrically insulating material, has a top surface and a bottom surface opposite to the top surface, and is formed with a plurality of spaced-apart through holes. Each of the through holes is defined by an interior wall surface and penetrates the top and bottom surfaces.

Each of the layered active metal parts is formed at least upon a respective one of the interior wall surfaces.

The layered electrodes are respectively formed on the layered active metal parts.

The reaction confinement layer is disposed on the substrate and confines a reactor space over a region of the substrate where the through holes are formed.

The electrochemical reactive layer is disposed in the reactor space and is electrically coupled to the layered electrodes.

The cover piece is disposed to cover the electrochemical reactive layer.

According to another aspect of the present invention, an electrochemical biosensor may be adapted for use with a measuring device and include a substrate, an electrochemical reactive layer, a plurality of electrically-conductive vias and a cover piece.

The substrate is made of an electrically insulating material, has a top surface and a bottom surface opposite to the top surface, and is formed with a plurality of spaced-apart through holes. Each of the through holes is defined by an interior wall surface and penetrates the top and bottom surfaces.

The electrochemical reactive layer is disposed on the substrate.

Each of the electrically-conductive vias is formed at least inside a respective one of the interior wall surfaces and has a bottom part that is proximal to the bottom surface of the substrate and that is configured to have electrical contact with a corresponding portion of the measuring device, and a top part that is proximal to the top surface of the substrate and that is electrically coupled to the electrochemical reactive layer.

The cover piece is disposed to cover the electrochemical reactive layer.

According to yet another aspect of the present invention, a method for producing an electrochemical biosensor may include: forming a plurality of spaced-apart through holes in an electrically insulating substrate, the through holes penetrating top and bottom surfaces of the electrically insulating substrate; forming a plurality of layered active metal parts respectively in the through holes; forming a plurality of layered electrodes respectively on the layered active metal parts; and forming an electrochemical reactive layer on one of the top and bottom surfaces of the substrate to electrically connect the layered electrodes.

According to a further aspect of the present invention, a method for producing an electrode of an electrochemical biosensor may include steps of: forming a through hole in an electrically insulating substrate; activating at least a portion of an interior wall surface within the through hole; and forming a layer of metal-containing electrode material on the portion of the interior wall surface to produce the electrode.

BRIEF DESCRIPTION OF THE DRAWINGS

Other features and advantages of the present invention will become apparent in the following detailed description of the exemplary embodiments with reference to the accompanying drawings, of which.

DETAILED DESCRIPTION OF THE EXEMPLARY EMBODIMENTS

Figure 1:
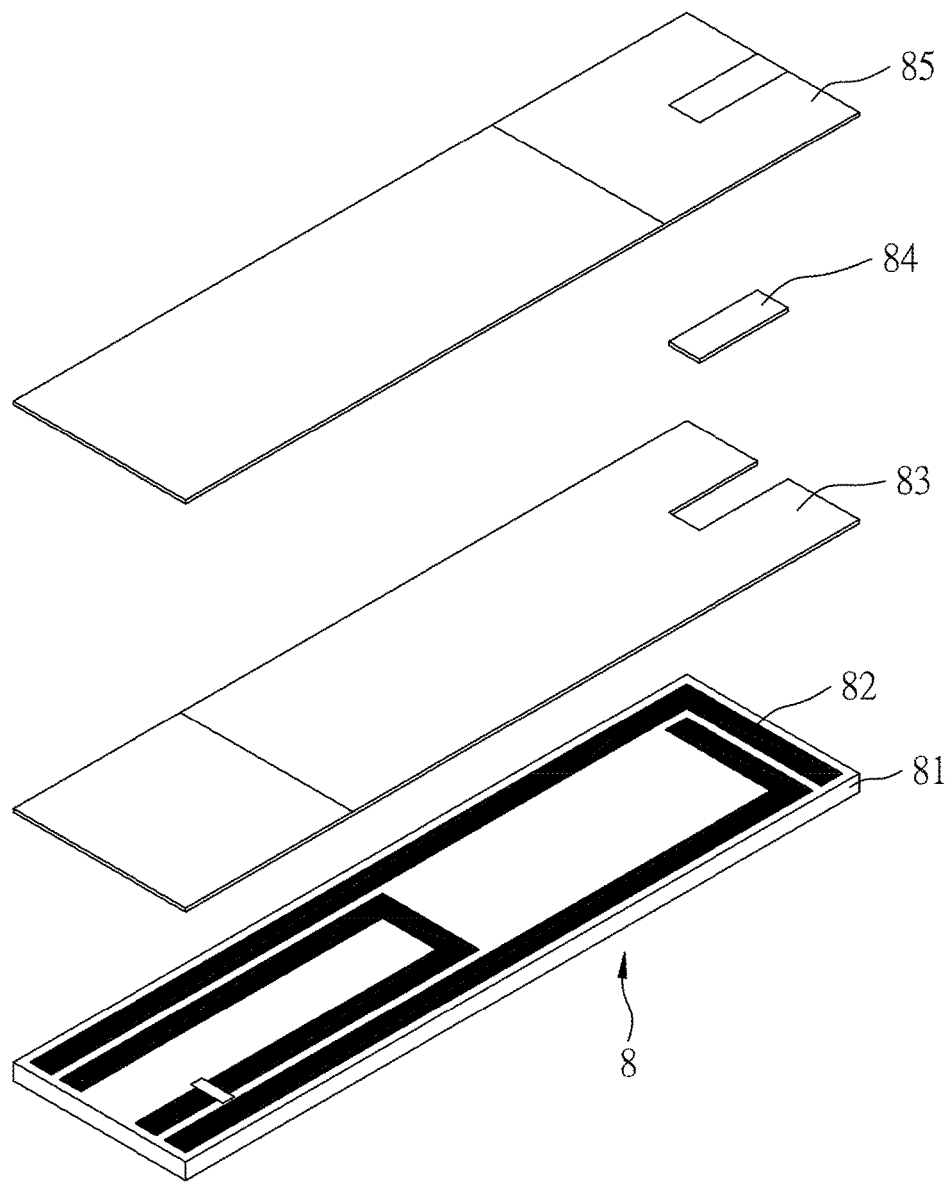
FIG. 1 is an exploded perspective view, illustrating an electrochemical biosensor.
Figure 2:
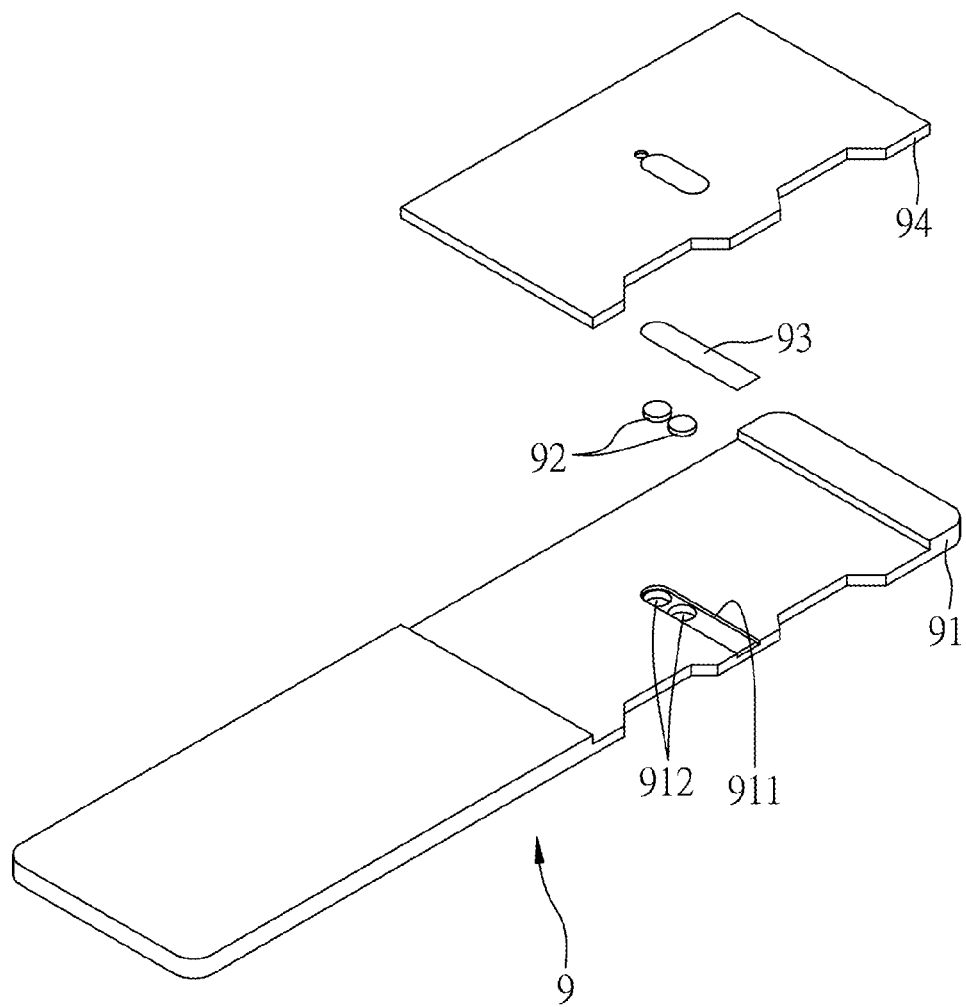
FIG. 2 is an exploded perspective view, illustrating another electrochemical biosensor.

Before the present invention is described in greater detail, it should be noted that like elements are denoted by the same reference numerals throughout the disclosure.

Referring to FIGS. 3 to 6, a first exemplary embodiment of an electrochemical biosensor 1 according to the present invention is shown to include a substrate 2, a plurality of layered active metal parts 3, a plurality of layered electrodes 4, a reaction confinement layer 5, an electrochemical reactive layer 6, and a cover piece 7.

The substrate 2, which has a top surface 21 and a bottom surface 22 opposite to the top surface 21, is formed with a plurality of spaced-apart through holes 231. Each of the through holes 231 is defined by an interior wall surface 23 and penetrates the top and bottom surfaces 21, 22. In this embodiment, the substrate 2 is made of an electrically insulating material and is configured in a rectangular shape. Examples of the electrically insulating material may include, but are not limited to, polyethylene (PE), polyimide (PI) and polycarbonate (PC). In this embodiment, the number of the through holes 231 formed in the substrate 2 is two, but the number of the through holes 231 according to the present invention is not limited to what is disclosed in this embodiment.

Figure 5:
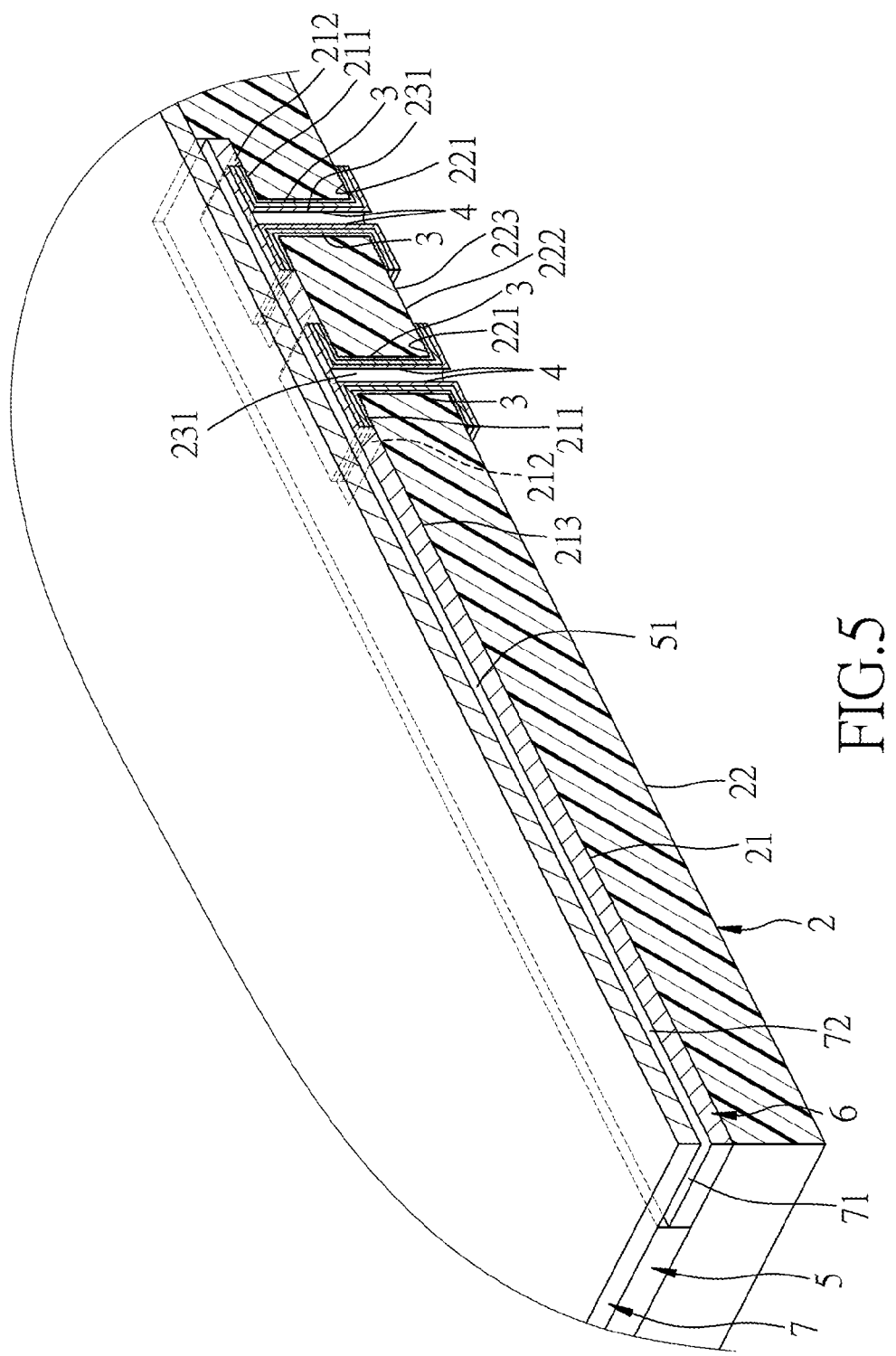
FIG. 5 is a fragmentary sectional view taken along line V-V in FIG. 4.

As shown in FIG. 5, in this embodiment, the top surface 21 of the substrate 2 has a plurality of top to-be-plated zones 211 that respectively extend around the through holes 231, and a plurality of top separating zones 212 that extend respectively around the top to-be-plated zones 211 and that respectively isolate the top to-be-plated zones 211 from a top plating-free zone 213 of the top surface 21. Similarly, the bottom surface 22 of the substrate 2 has a plurality of bottom to-be-plated zones 221 that respectively extend around the through holes 231, and a plurality of bottom separating zones 222 that extend respectively around the bottom to-be-plated zones 221 and that respectively isolate the bottom to-be-plated zones 221 from a bottom plating-free zone 223 of the bottom surface 22. In this embodiment, the top and bottom to-be-plated zones 211, 221, and the interior wall surfaces 23 are roughened, but it should be noted that, in other embodiments, the top and bottom to-be-plated zones 211, 221, and/or the interior wall surfaces 23 may be partially roughened or not roughened at all.

Figure 6:
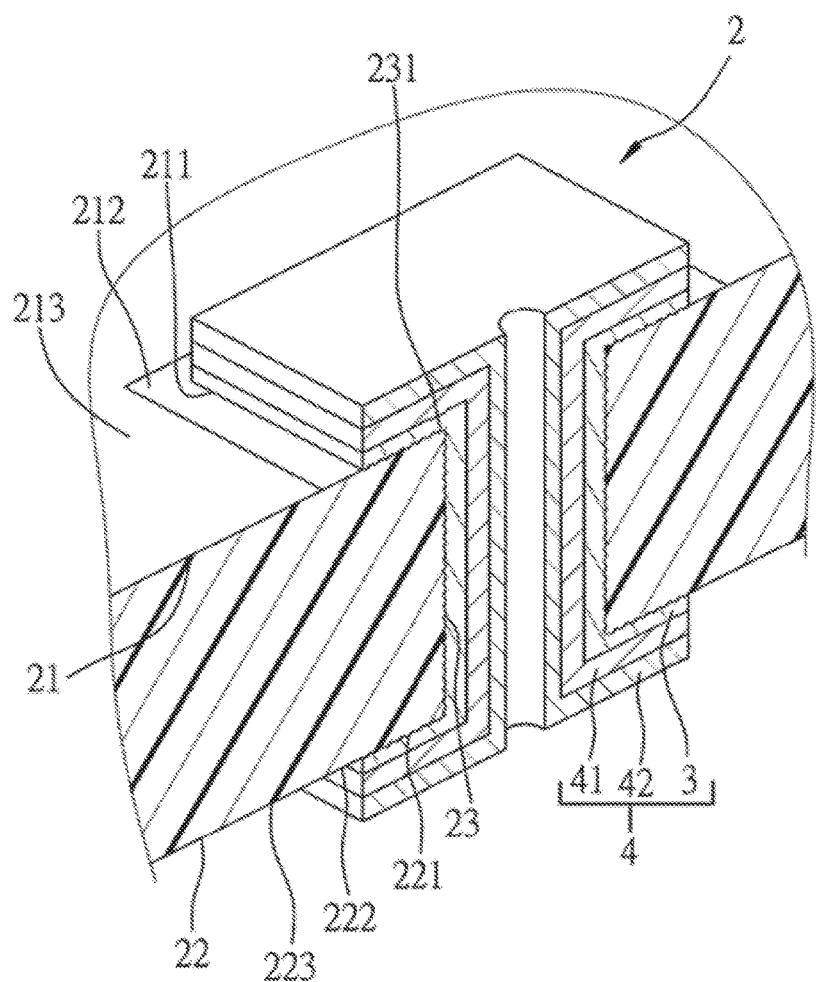
FIG. 6 is a fragmentary sectional view, illustrating a layered electrode formed in and beyond a through hole.

As shown in FIG. 6, each of the layered active metal parts 3 is formed at least upon a respective one of the interior wall surfaces 23 of the substrate 2 and corresponds in position to a respective one of the through holes 231. In this embodiment, each of the layered active metal parts 3 extend outwardly from the respective one of the interior wall surfaces 231 to cover the top and bottom to-be-plated zones 211, 221 which surround the respective one of the interior wall surfaces 231. In some embodiments, the layered active metal parts 3 may be made of a material that is selected from the group consisting of palladium, rhodium, platinum, iridium, osmium, gold, nickel and combinations thereof.

Referring to FIGS. 5 and 6, the layered electrodes 4 are made of a metal-containing electrode material and are respectively formed on the layered active metal parts 3, which correspond respectively in position to the through holes 231. In this embodiment, each of the layered electrodes 4 includes a first layered metal part 41 bonded to the respective one of the layered active metal parts 3, and a second layered metal part 42 bonded to the first layered metal part 41 and opposite to the respective one of the layered active metal parts 3. In some embodiments, the first layered metal parts 41 of the layered electrodes 4 may be made of a material selected from the group consisting of copper, nickel, silver and combinations thereof. In some embodiments, the second layered metal parts 42 of the layered electrodes 4 may be made of a material selected from the group consisting of gold, nickel, titanium and combinations thereof. In such embodiments, gold is more preferred owing to its relatively high affinity to biological reagents. It should be noted that, in some embodiments, the layered electrodes 4 may be single-layered, for instance, and have only the first layered metal parts 41. In some other embodiments, each of the layered electrodes 4 may be configured in a multilayered structure having a plurality of stacking layers made of identical material by similar processes. In this embodiment, as shown in FIG. 6, each of the layered electrodes 4 partially fills the respective one of the through holes 231 and has an annular cross-section inside the respective one of the through holes 231. However, the through holes 231 may be completely filled up by the layered electrodes 4 in other embodiments in accordance with the present invention.

Figure 3:
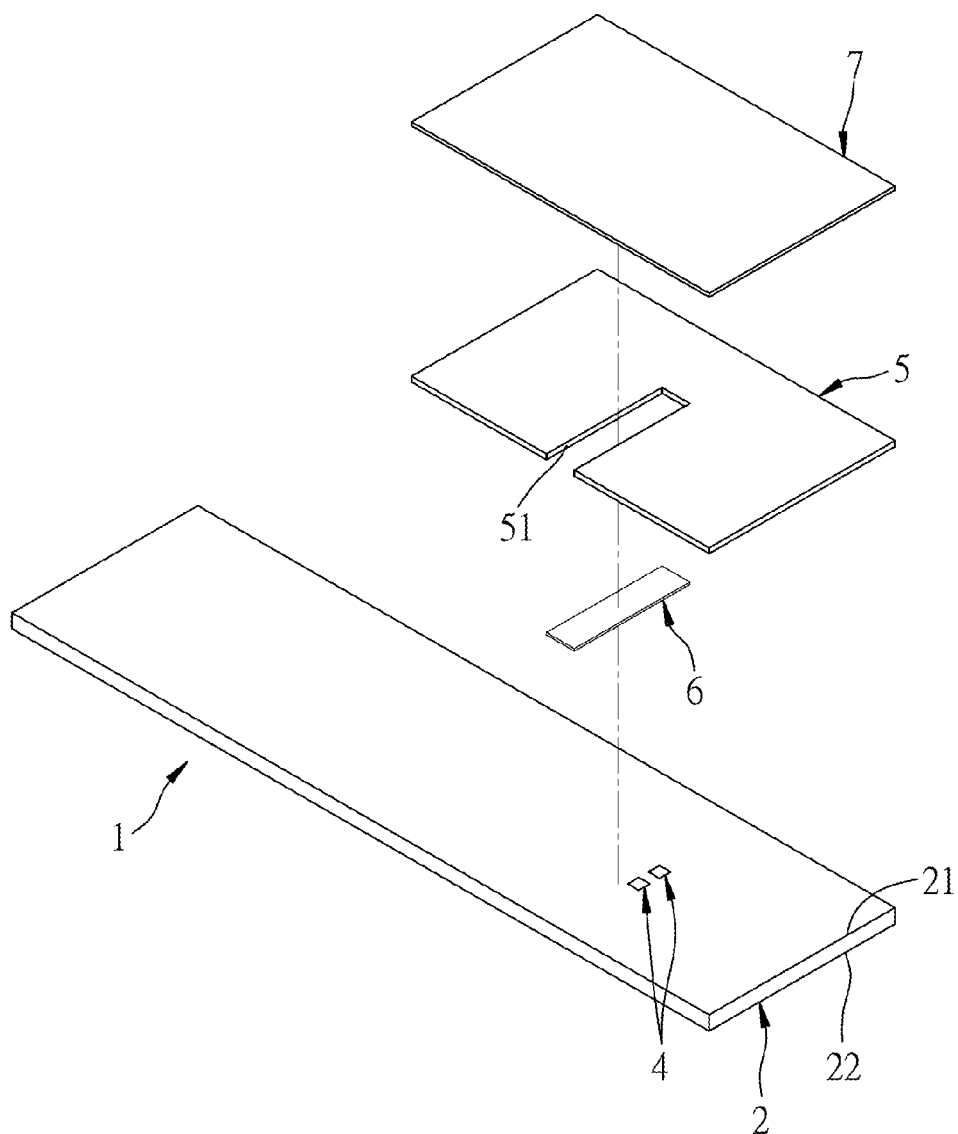
FIG. 3 is a partly exploded perspective view, illustrating one embodiment of an electrochemical biosensor.
Figure 4:
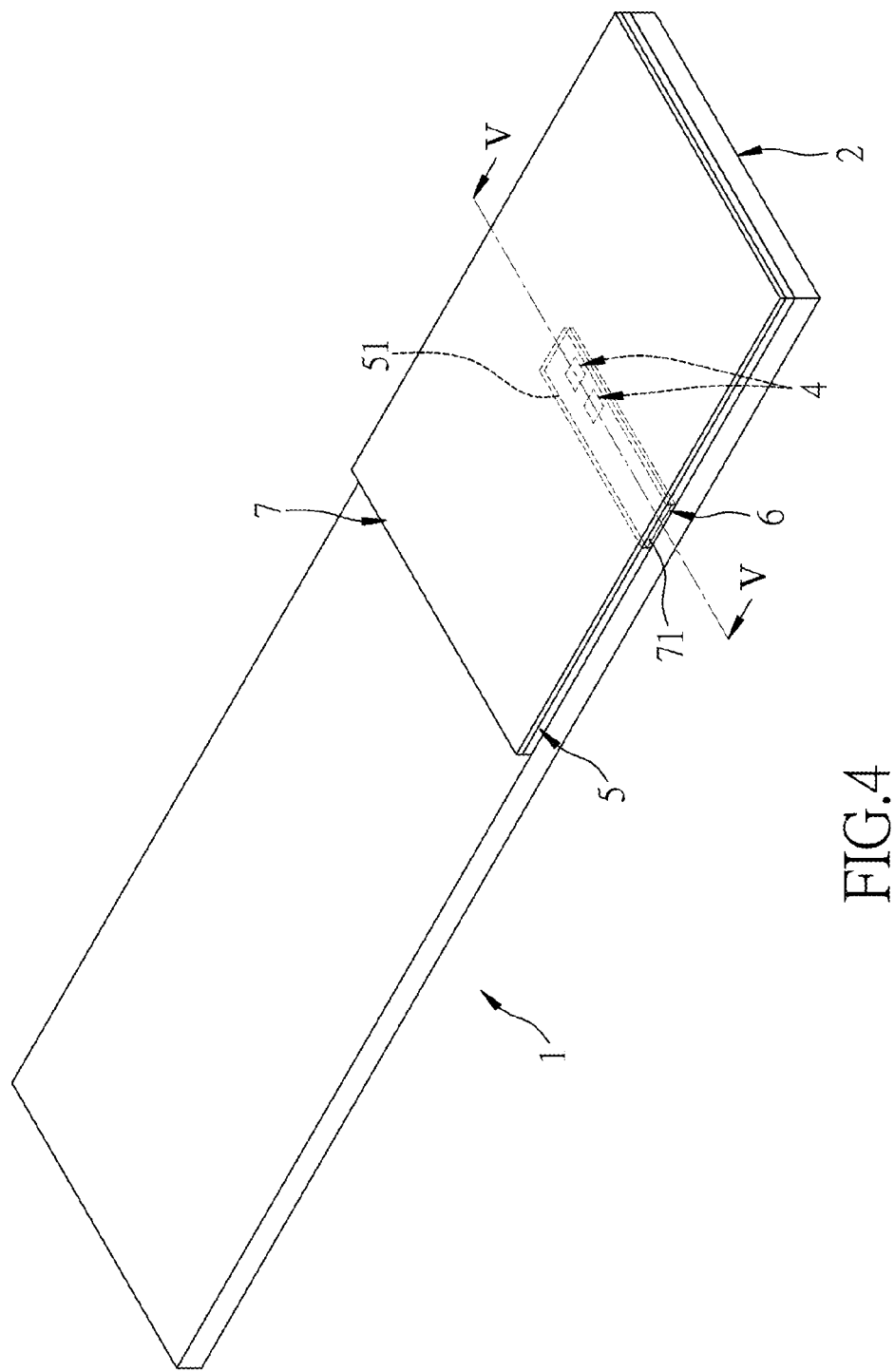
FIG. 4 is a perspective view of one embodiment.

Referring to FIGS. 3 to 5, the reaction confinement layer 5 is disposed on the top surface 21 of the substrate 2 and is formed with a reactor space 51 over a region of the substrate 2 where the through holes 231 are formed. In this embodiment, the reaction confinement layer 5 is configured in a rectangular shape and has a bottom surface that is adhered to the top surface 21 of the substrate 2. As shown in FIG. 4, a width of the reaction confinement layer 5 is substantially identical to that of the substrate 2. It should be noted that, in some embodiments, the substrate 2 and the reaction confinement layer 5 may be integrally formed as one piece. As shown in FIG. 3, in this embodiment, the reactor space 51 is configured as a rectangular notch formed at a longitudinal side of the reaction confinement layer 5 to confine the electrochemical reactive layer 6 therein.

As shown in FIG. 5, the electrochemical reactive layer 6 is disposed in the reactor space 51 to cover the layered electrodes 4 and is electrically coupled to the layered electrodes 4. The electrochemical reactive layer 6 may be electrochemically reactive with an analyte in a sample liquid (not shown) introduced into the reactor space 51, so as to generate an output electrical signal that may be transmitted to the layered electrodes 4, to which a coupling portion of an external measuring device may be coupled for reading the output electrical signal.

The cover piece 7 is disposed to cover the electrochemical reactive layer 6. In this embodiment, a bottom surface of the cover piece 7 is adhered to a top surface of the reaction confinement layer 5. In this embodiment, the cover piece 7 is configured in a rectangular shape and has a length and a width substantially identical to those of the reaction confinement layer 5. The reactor space 51 of the reaction confinement layer 5 is further confined by the substrate 2, the electrochemical reactive layer 6 and the cover piece 7 to form a sample-receiving space 72 for receiving the sample liquid. In addition, the substrate 2, the reaction confinement layer 5, and the cover piece 7 may cooperatively define a sample inlet 71 at the longitudinal side of the substrate 2 for introduction of the sample liquid into the sample-receiving space 72.

By forming the layered active metal parts 3 on the interior wall surfaces 231 and on the top and bottom to-be-plated zones 211, 221, the layered electrodes 4, which are respectively formed on the layered active metal parts 3, can be tightly and firmly bonded to the substrate 2 via the layered active metal parts 3. Moreover, the layered active metal parts 3 and the layered electrodes 4 constitute a plurality of electrically conductive vias each of which is at least formed along and inside a respective one of the through holes 231. Each of the electrically conductive vias has a top part that is proximal to the top surface 21 and that is electrically coupled to the electrochemical reactive layer 5, and a bottom part that is proximal to the bottom surface 22 of the substrate 2 and that is configured to have electrical contact with the coupling portion of the external measuring device (not shown), so that the electrical output signal resulting from the electrochemical reaction between the analyte and the electrochemical reactive layer 6 can be transmitted through the electrically conductive vias to the coupling portion of the external measuring device. As such, a process for assembling electrodes to the substrate can thereby be omitted, so as to simplify the manufacturing process of the electrochemical biosensor 1 and to enhance production efficiency thereof.

Figure 7:
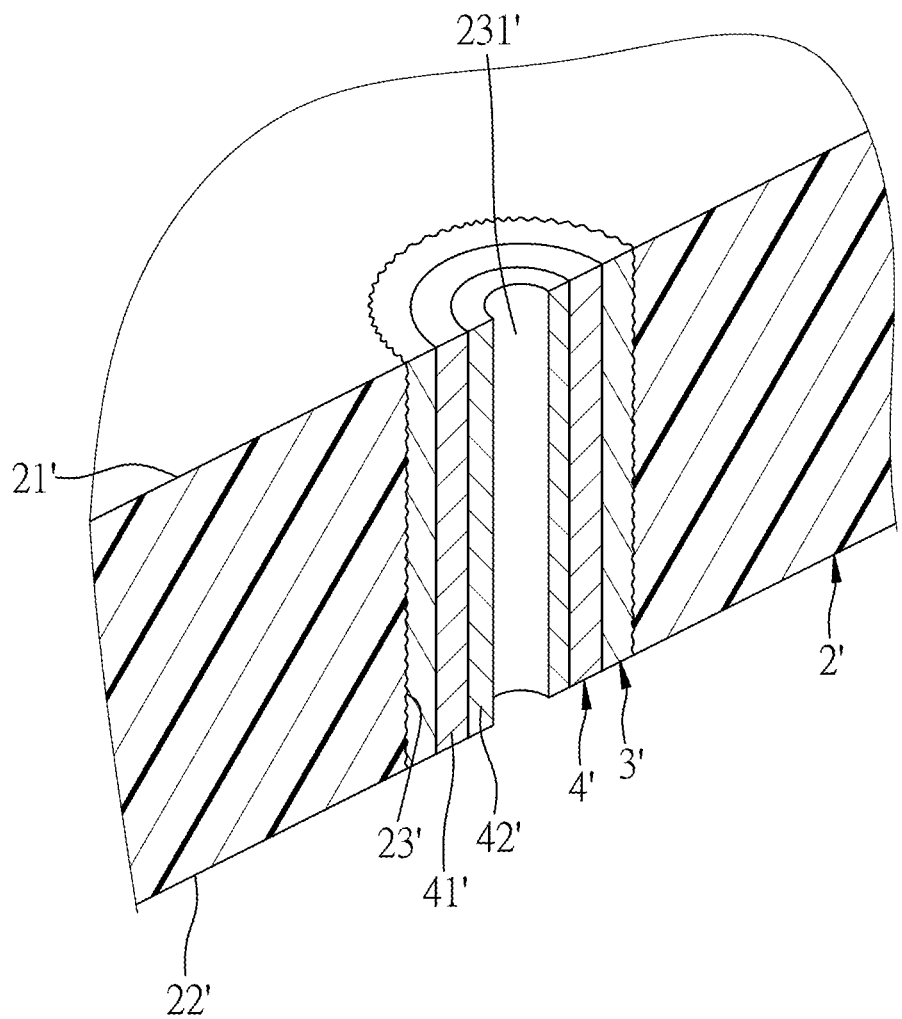
FIG. 7 is a fragmentary sectional view of one embodiment, illustrating the electrochemical biosensor.

Referring to FIG. 7, a second exemplary embodiment of the electrochemical biosensor according to the present invention is shown to be similar to that of the first embodiment with the difference therebetween residing in that, in the second exemplary embodiment, the layered active metal parts 3' (only one is shown) and the layered electrodes 4' (only one is shown) are merely formed on the interior wall surfaces 23' (only one is shown), respectively, and are limited from extending therebeyond. That is to say, the electrically-conductive vias, which are composed of the layered active metal parts 3' and the layered electrodes 4', are disposed respectively inside the through holes 231' (only one is shown) and are flush with the top and bottom surfaces 21', 22' of the substrate 2'. In this embodiment, the coupling portion of the external measuring device can be configured to have protrusions for enhancement of electrical contact with the electrically-conductive vias.

Figure 8:
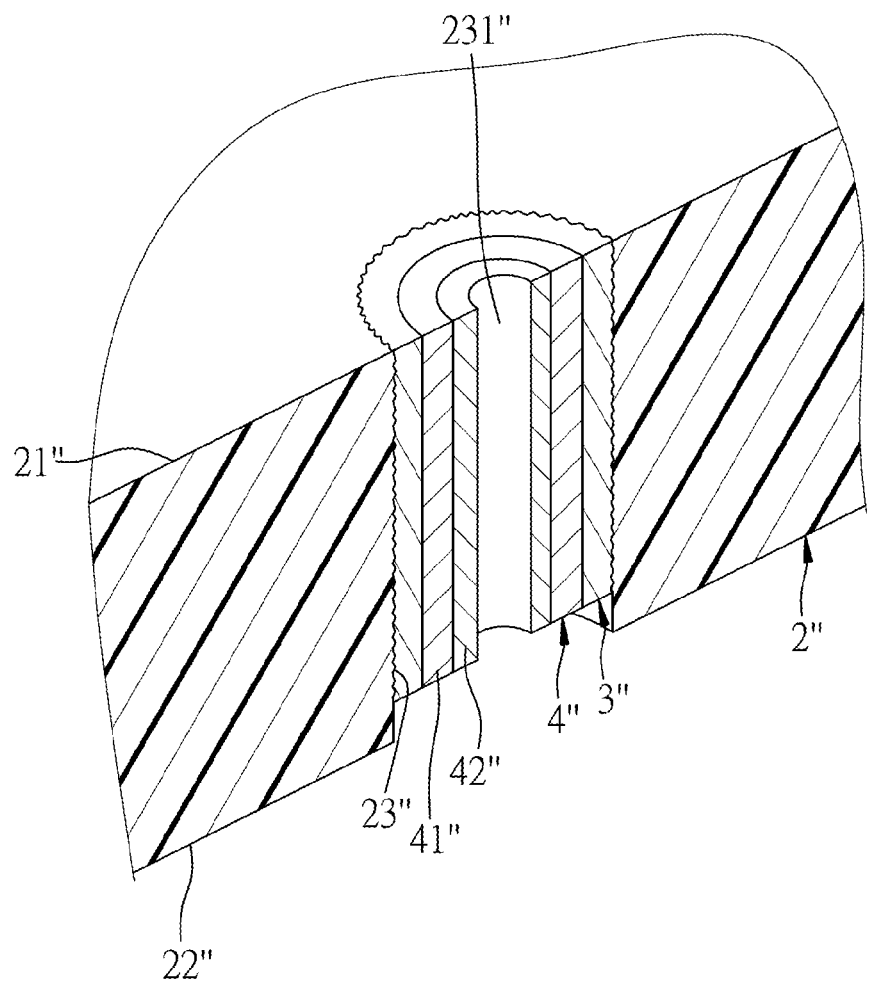
FIG. 8 is a fragmentary sectional view of one embodiment, illustrating another configuration of the layered electrode.

Referring to FIG. 8, a third exemplary embodiment of the electrochemical biosensor is shown to be similar to the second exemplary embodiment. The difference between the second and third exemplary embodiments resides in that each layered active metal parts 3" in the third exemplary embodiment is limited from extending beyond the respective one of the interior wall surfaces 23" and is not flush with the bottom surface 22" of the substrate 2". It should be noted that, in other embodiments, the layered active metal parts 3" (only one is shown) may be limited from extending beyond the interior wall surfaces 23" (only one is shown) and be not flush with the top surface 21"(or be not flush with both the top and bottom surfaces 21", 22"). Similar to the second exemplary embodiment, the coupling portion of the external measuring device may be configured to have protrusions for enhancement of electrical contact with the electrically-conductive vias.

Figure 9:
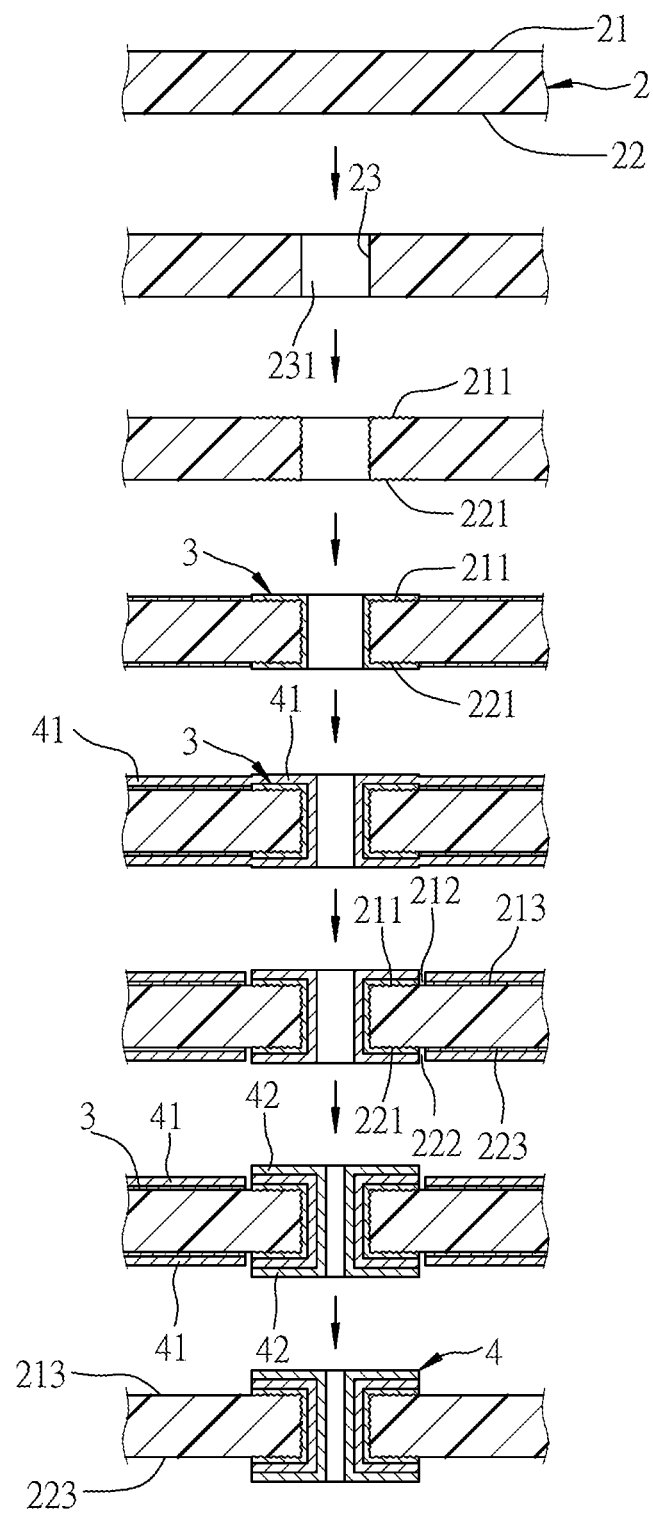
FIG. 9 is a schematic flow diagram of forming the layered electrode of the electrochemical biosensor of one embodiment.
Figure 10:
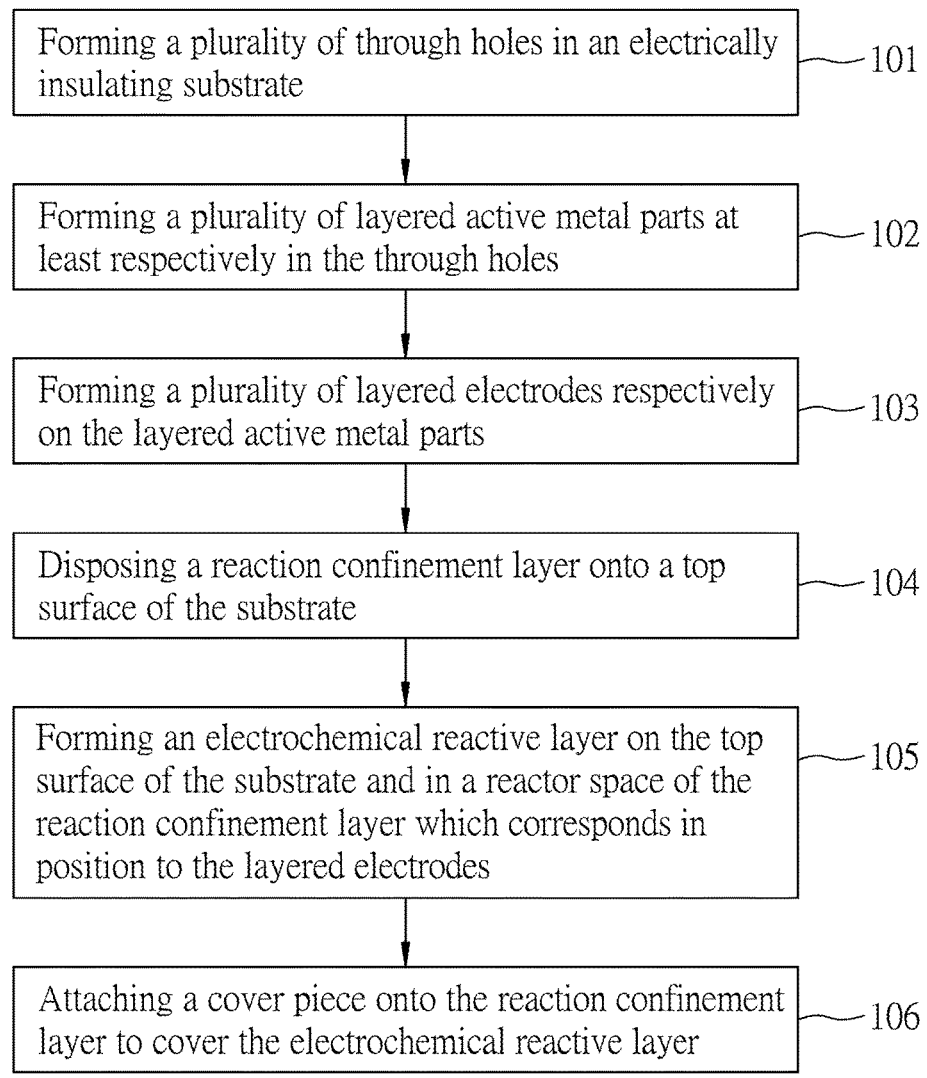
FIG. 10 is a flow chart illustrating a method for producing the electrochemical biosensor of one embodiment.

Referring to FIGS. 9 and 10, a method for producing the electrochemical biosensor of the first exemplary embodiment according to the present invention includes steps as follows.

Step 101: forming a plurality of the spaced-apart through holes 231 in the electrically insulating substrate 2. Note that for the sake of simplicity, only one through hole 231 and components/parts associated with said one through hole 231 are depicted in FIG. 9. The through holes 231 penetrate top and bottom surfaces 21, 22 of the substrate 2. In this embodiment, the forming of the through holes 231 is conducted using laser. However, in other embodiments, the forming of the through holes 231 may be conducted using other techniques, such as mechanical punching.

Step 102: forming a plurality of the layered metal parts 3 in the through holes 231 and on peripheral surface areas of the top and bottom surfaces 21, 22 which respective extend around the through holes 231. The top and bottom to-be-plated zones 211, 221 are respectively located on the peripheral surface areas of the top and bottom surfaces 21, 22 and have the layered active metal parts 3 formed thereon. In this embodiment, the forming of the layered active metal parts 3 includes roughening the interior wall surfaces 23 and the top and bottom to-be-plated zones 211, 221, followed by immersing the substrate 2 into an active metal solution. In this embodiment, the active metal solution is a Palladium-Tin colloid solution and has a palladium concentration ranging from 1 ppm to 750 ppm. Since the interior wall surfaces 23 and the top and bottom to-be-plated zones 211, 221 are roughened, the layered active metal parts 3 formed on the top and bottom to-be-plated zones 211, 221 may be thicker than active metal layers formed on other portions of the peripheral surface areas of the top and bottom surfaces 21, 22 (see FIG. 9). As mentioned hereinbefore, the interior wall surfaces 23 and the top and bottom to-be-plated zones 211, 221 may be partially roughened or not roughened at all in other embodiments according to the present invention.

Step 103: forming a plurality of the layered electrodes 4 respectively on the layered active metal parts 3. In this embodiment, the forming of the layered electrodes 4 includes forming a plurality of the first layered metal parts 41 respectively on the layered active metal parts 3, removing a portion of each of the layered active metal parts 3 and each of the first layered metal parts 41 from a respective one of the peripheral surface areas, and forming a plurality of second layered metal parts 42 respectively on the first layered metal parts 41 remaining on the top and bottom to-be-plated zones 211, 221.

The forming of the first layered metal parts 41 may be conducted by electroless plating. In this embodiment, the forming of the first layered metal parts 41 is conducted by immersing the substrate 2 into an electroless-plating cooper solution at a temperature ranging from 50° C. to 55° C. for 2 to 5 minutes.

The partial removal of the first layered metal parts 41 and the active metal parts 3 is conducted by laser etching, so that the top and bottom to-be-plated zones 211, 221 are isolated respectively by the top and bottom separating zones 212, 222 from the top and bottom plating-free zones 213, 223, respectively, and so that the top and bottom separating zones 212, 222 are free of the layered active metal parts 3 and the first layered metal parts 41. In this embodiment, the laser power ranges from 5 to 10 watts with a pulse frequency ranging from 20 to 50 kHz.

In this embodiment, the forming of the second layered metal parts 42 is conducted by electroplating. By virtue of the top and bottom separating zones 212, 222, the second layered metal parts 42 may be merely formed on the layered active metal parts 3 which are formed on the top and bottom to-be-plated zones 211, 221 and on the interior wall surfaces 23.

After the forming of the second layered metal parts 42, those of the layered active metal parts 3 and the first layered metal parts 41, which are formed on the top and bottom plating-free zones 213, 223 are removed using, for example, chemical etching techniques.

Step 104: disposing the reaction confinement layer 5 onto the top surface 21 of the substrate 2 to confine the reactor space 51 over the region of the substrate 2, where the through holes 231 and the layered electrodes 4 are formed (see FIG. 3). In this embodiment, the reactor space 51 has an open end that is flush with a longitudinal side of the substrate 2. It should be noted that in other embodiments, the reaction confinement layer 5 and the substrate 2 may be integrally formed as one piece.

Step 105: forming the electrochemical reactive layer 6 on the top surface 21 of the substrate 2 and in the reactor space 51 to electrically connect the layered electrodes 4 (see FIG. 3). In this embodiment, the forming of the electrochemical reactive layer 6 is conducted by distributing a layer of electrochemical reagents onto the top surface 21 of the substrate 2 in the reactor space 51 to cover the layered electrodes 4.

Step 106: attaching the cover piece 7 onto the reaction confinement layer 5 to cover the electrochemical reactive layer 6 and the layered electrodes 4 (see FIG. 3).

It is worth noting that, in some embodiments, the forming of the layered active metal parts 3 may be conducted by screen printing. In such embodiments, the screen printing includes applying an active metal solution onto the top and bottom to-be-plated zones 211, 221 and allowing the active metal solution to flow into the through holes 231, thereby forming the layered active metal parts 3 only on the top and bottom to-be-plated zones 211, 221 and on the interior wall surfaces 23. Thus, no top and bottom separating zones 212, 222 are needed in such embodiments in accordance with the present invention.

In addition, instead of the screen printing, the layered active metal parts 3 may be formed using laser direct structuring techniques (developed by LPKF Laser& Electronics, AG), i.e., using laser to activate a layer of metal-ion-containing plastic material formed on the interior wall surfaces 23 and the top and bottom to-be-plated zones 211, 221.

A method for producing the layered electrode of the electrochemical biosensor of the second exemplary embodiment according to the present invention is similar to that of the first exemplary embodiment and includes the following steps of, referring to FIG. 7, forming a plurality of the spaced-apart through holes 231' on the insulating substrate 2'; forming a plurality of the layered active metal parts 3' respectively on the interior wall surfaces 23' which respectively define the through holes 231'; and forming a plurality of the layered electrodes 4' respectively on the layered active metal parts 3'. The forming of the layered active metal parts 3' includes roughening the interior wall surfaces 23' by laser, and immersing the substrate 2' into an active metal solution to form the layered active metal parts 3'. The forming of the layered electrodes 4' includes forming a plurality of the first layered metal parts 41' onto the layered active metal parts 3' by electroless plating, removing the first layered metal parts 41' and the layered active metal parts 3' on the top and bottom surfaces 21', 22', and forming a plurality of second layered metal parts 42' onto the remaining first layered metal parts 41' (i.e., those on the interior wall surfaces 23') by electroplating, so as to obtain the layered electrodes 4'.

To sum up, by virtue of the electrically-conductive vias, the electrical output signal resulting from the electrochemical reaction between the analyte in the sample liquid and the electrochemical reactive layer 6 can be transmitted to the coupling portion of the external measuring device. As such, the production cost for the electrochemical biosensor of the present invention can be effectively lowered, and attenuation and interference of the electrical output signal can also be reduced. Moreover, the method for producing the electrochemical biosensor according to the present invention may assure relatively stable bonding between the layered electrodes 4/4'/4" and the substrate 2/2'/2", as well as to achieve a relatively simple manufacturing process.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An electrochemical biosensor, comprising: a substrate made of an insulating material, that has a top surface and a bottom surface that is separated by a thickness from the top surface;
   a plurality of spaced-apart through holes, wherein each of the spaced-apart through holes defines an interior wall surface, and the plurality of spaced-apart through holes penetrate the top surface and bottom surface of the substrate;
   a reaction confinement layer disposed on the substrate that defines a reactor space over a region of the substrate, wherein the region includes the plurality of spaced-apart through holes;
   an electrochemical reactive layer disposed in the reactor space;
   multilayered stacked structures formed on the interior wall surface of each of the plurality of spaced-apart through holes, wherein the multilayered stacked structures include:
   a layered active metal part formed on the interior wall surface, and;
   an electrode formed the layered active metal part on a side opposite to the interior wall surface, wherein the electrode electrically couples to the electrochemical reactive layer of the substrate;
   a cover piece that is disposed to cover the electrochemical reactive layer,
   wherein each of the multilayered stacked structures formed inside each of the plurality of spaced-apart through holes has a length that is not greater than the thickness of the substrate,
   and wherein there is a second hole in each through-hole coaxial with the respective through-hole having the same length as the respective multilayered stacked structure.

2. The electrochemical biosensor according to claim 1, wherein the interior wall surface of each of the plurality of spaced-apart through holes has a roughened surface.

3. The electrochemical biosensor according to claim 1, wherein each of the multilayered stacked structures formed inside each of the plurality of spaced-apart through holes further include:
 a first layered metal part that is bonded to the layered active metal part; and
 a second layered metal part that is bonded to the first layered metal part and that is opposite to the first layered metal part.

4. The electrochemical biosensor according to claim 3, wherein:
 the first layered metal part is made of a material that is selected from the group consisting of copper, nickel, silver and combinations thereof; and
 the second layered metal part is made of a material that is selected from the group consisting of gold, nickel, titanium and combinations thereof.

* * * * *